United States Patent [19]

Herber

[11] 4,056,480
[45] Nov. 1, 1977

[54] HYDRAULIC FLUIDS

[75] Inventor: John F. Herber, St. Louis, Mo.

[73] Assignee: Monsanto Company, St. Louis, Mo.

[21] Appl. No.: 585,636

[22] Filed: June 10, 1975

[51] Int. Cl.$^2$ .................. C10M 3/40; C10M 3/38
[52] U.S. Cl. ............................ 252/78.5; 260/928; 260/929; 260/930
[58] Field of Search .............. 252/78, 49.8, 49.9, 252/78.5, 78.1; 260/928, 929, 930

[56] References Cited

U.S. PATENT DOCUMENTS

| | | | |
|---|---|---|---|
| 2,632,767 | 3/1953 | Smith et al. | 252/49.8 X |
| 2,686,760 | 8/1954 | Watson | 252/75 |
| 2,736,737 | 2/1956 | Morris | 252/46.6 X |
| 2,978,478 | 4/1961 | Sandner et al. | 252/78 X |
| 3,081,331 | 3/1963 | Friedman | 252/49.8 X |
| 3,954,918 | 5/1976 | Hotten | 260/928 X |

Primary Examiner—Harris A. Pitlick
Attorney, Agent, or Firm—William H. Duffey

[57] ABSTRACT

Improved hydraulic fluids contain at least one compound represented by the structure:

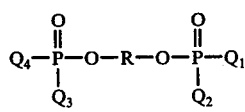

where $Q_1$ is —O—$R_1$ or

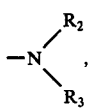

$Q_2$ is —O—$R_4$ or

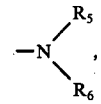

$Q_3$ is —O—$R_7$ or

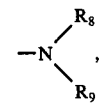

and $Q_4$ is —O—$R_{10}$ or

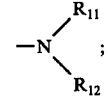

R is selected from the group consisting of non-phenolic ether residue, non-phenolic thioether residue, non-phenolic polyether residue, linear alkyl, branched alkyl, cyclic alkyl, substituted cyclic alkyl, cycloalkyl, substituted cycloalkyl and non-phenolic alkyl-aryl, containing from 1 to 16 carbon atoms; provided that the —O—R—O— portion of the structure is non-phenolic; $R_1$, $R_2$, $R_3$, $R_4$, $R_5$, $R_6$, $R_7$, $R_8$, $R_9$, $R_{10}$, $R_{11}$ and $R_{12}$ are individually selected from the group consisting of linear alkyl, branched alkyl, cyclic alkyl, non-phenolic alkylaryl or substituted cyclic alkyl, containing from 1 to 12 carbon atoms and can be the same or different in any combination; $R_2$ and $R_3$ together can form a heterocyclic ring optionally interrupted by hetero atoms selected from the group consisting of oxygen, sulfur and nitrogen; $R_5$ and $R_6$ together can form a heterocyclic ring optionally interrupted by hetero atoms selected from the group consisting of oxygen, sulfur and nitrogen; $R_8$ and $R_9$ together can form a heterocyclic ring optionally interrupted by hetero atoms selected from the group consisting of oxygen, sulfur and nitrogen; $R_{11}$ and $R_{12}$ together can form a heterocyclic ring optionally interrupted by hetero atoms selected from the group consisting of oxygen, sulfur and nitrogen.

4 Claims, No Drawings

HYDRAULIC FLUIDS

DESCRIPTION OF THE PRIOR ART

Many different types of materials are utilized as functional fluids and functional fluids are used in many different types of applications. Such fluids have been used as electronic coolants, atomic reactor coolants, diffusion pump fluids, synthetic lubricants, damping fluids, bases for greases, force transmission fluids (hydraulic fluids), heat transfer fluids, die-casting release agents in metal extrusion processes and as filter mediums for air conditioning systems. Because of the wide variety of applications and the varied conditions under which functional fluids are utilized, the properties desired in a good functional fluid necessarily vary with the particular application in which it is to be utilized with each individual application requiring a functional fluid having a specific class of properties.

Of the foregoing the use of functional fluids as heat transfer fluids and hydraulic fluids, particularly aircraft hydraulic fluids, has posed what is probably the most difficult area of application. Thus, the requirements of a heat transfer fluid are as follows: the fluid should be liquid over a wide temperature range, in general having low vapor pressure so as to be utilized at atmospheric pressure. Such fluid should be operable as a heat transfer media over an extended period of time at given temperatures and should in addition be fire resistant, non-toxic and exhibit a high degree of thermal and hydrolytic stability. The requirements for an aircraft hydraulic fluid can be described as follows: hydraulic power systems of aircraft for operating various mechanisms of an airplane impose stringent requirements on the hydraulic fluid used. Not only must the hydraulic fluid for aircraft meet stringent functional and use requirements but in addition such fluid should be as highly fire resistant as possible and must be sufficiently fire resistant to satisfy aircraft requirements for fire resistance. The viscosity characteristics of the fluid must be such that it may be used over a wide temperature range; that is, adequately high viscosity at high temperatures, low viscosity at low temperatures and a low rate of change of viscosity with temperature. Its pour point should be low. Its volatility should be low at elevated temperatures of use and the volatility should be balanced; that is, selective evaporation or volatilization of any important components should not take place at the high temperatures of use. It must possess sufficient lubricity and mechanical stability to enable it to be used in the self-lubricated pumps, valves, etc. employed in the hydraulic systems of aircraft which are exceedingly severe on the fluid used. It should be thermally and chemically stable in order to resist oxidation and decomposition so that it will remain uniform in the conditions of use and be able to resist the loss of desired characteristics due to high and sudden changes of pressure and temperature, high shearing stresses, and contact with various metals. It should also not deteriorate the gaskets or packing of the hydraulic system. It must not adversely affect the materials of which the system is constructed, and in the event of a leak, it should not adversely affect the various parts of the airplane with which it may accidentally come in contact, such as electrical wire insulation and paint. It should not be toxic or harmful to personnel who may come in contact with it.

SUMMARY OF THE INVENTION

It is an object of this invention to provide an improved method of transmitting force from one point to another utilizng a hydraulic fluid as the force transmitting medium. It is another object of this invention to provide a new class of compounds.

The first of these objects is realized in an improved method of transmitting force from one point to another utilizing a hydraulic fluid as the force transmitting medium wherein the improvement comprises utilizing a hydraulic fluid containing at least one compound represented by the structure:

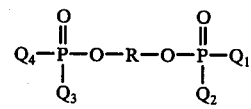

where $Q_1$ is $-O-R_1$ or

$Q_2$ is $-O-R_4$ or

$Q_3$ is $-O-R_7$ or

and $Q_4$ is $-O-R_{10}$ or

R is selected from the group consisting of non-phenolic ether residue, non-phenolic thioether residue, non-phenolic polyether residue, non-phenolic polythioether residue, linear alkyl, branched alkyl, cyclic alkyl, substituted cyclic alkyl, cycloalkyl, substituted cycloalkyl and non-phenolic alkylaryl, containing from 1 to 16 carbon atoms; provided that the $-O-R-O-$ portion of the structure is non-phenolic; $R_1$, $R_2$, $R_3$, $R_4$, $R_5$, $R_6$, $R_7$, $R_8$, $R_9$, $R_{10}$, $R_{11}$ and $R_{12}$ are individually selected from the group consisting of linear alkyl, branched alkyl, cyclic alkyl, non-phenolic alkylaryl or substituted cyclic alkyl, containing from 1 to 12 carbon atoms and can be the same or different in any combination; $R_2$ and $R_3$ together can form a heterocyclic ring optionally interrupted by hetero atoms selected from the group consisting of oxygen, sulfur and nitrogen; $R_5$ and $R_6$ together can form a heterocyclic ring optionally interrupted by hetero atoms selected from the group consisting of oxygen, sulfur and nitrogen; $R_8$ and $R_9$ together can form a heterocyclic ring optionally interrupted by hetero atoms selected from the group consisting of oxygen, sulfur and nitrogen; $R_{11}$ and $R_{12}$ together can form a heterocyclic ring optionally interrupted by hetero atoms selected from the group consisting of oxygen, sulfur and nitrogen.

Another embodiment of this invention is an improved method of transmitting force from one point to another utilizing a hydraulic fluid as the force transmitting medium wherein the improvement comprises utilizing a hydraulic fluid containing at least one compound represented by the structure:

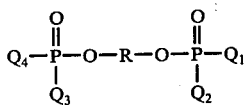

where $Q_1$ is —O—$R_1$ or

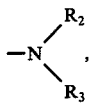

$Q_2$ is —O—$R_4$ or

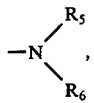

$Q_3$ is —O—$R_7$ or

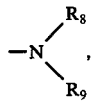

$Q_4$ is —O—$R_{10}$ or

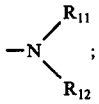

R is selected from the group consisting of non-phenolic ether residue, non-phenolic thioether residue, non-phenolic polyether residue, non-phenolic polythioether residue, linear alkyl, branched alkyl, cyclic alkyl, substituted cyclic alkyl and non-phenolic alkylaryl, R containing from 1 to 6 carbon atoms; provided that the —O—R—O— portion of the structure is non-phenolic; $R_1$, $R_2$, $R_3$, $R_4$, $R_5$, $R_6$, $R_7$, $R_8$, $R_9$, $R_{10}$, $R_{11}$ and $R_{12}$ each contain from 1 to 12 carbons and are individually selected from the group consisting of linear alkyl, branched alkyl, cyclic alkyl, non-phenolic alkylaryl, or substituted cyclic alkyl.

The new compounds of this invention are represented by the structure:

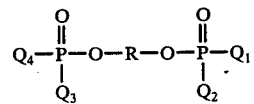

where $Q_1$ is —O—$R_1$ or

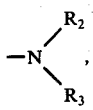

$Q_2$ is —O—$R_4$ or

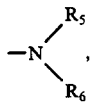

$Q_3$ is —O—$R_7$ or

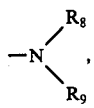

and $Q_4$ is —O—$R_{10}$ or

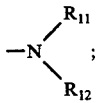

R is selected from the group consisting of non-phenolic thioether residue, nonphenolic polyether residue, non-phenolic polythioether residue, cyclic alkyl, substituted cyclic alkyl, cycloalkyl, substituted cycloalkyl, and non-phenolic alkylaryl containing from 2 to 16 carbon atoms; provided the —O—R—O— portion of the structure is non-phenolic; $R_1$, $R_2$, $R_3$, $R_4$, $R_5$, $R_6$, $R_7$, $R_8$, $R_9$, $R_{10}$, $R_{11}$ and $R_{12}$ are individually selected from the group consisting of linear alkyl, cyclic alkyl, substituted cyclic alkyl, non-phenolic alkylaryl and branched alkyl containing from 1 to 12 carbon atoms and can be the same or different in any combination; $R_2$ and $R_3$ together can form a heterocyclic ring optionally interrupted by hetero atoms selected from the group consisting of oxygen, sulfur and nitrogen; $R_5$ and $R_6$ together can form a heterocyclic ring optionally interrupted by hetero atoms selected from the group consisting of oxygen, sulfur and nitrogen; $R_8$ and $R_9$ together can form a heterocyclic ring optionally interrupted by hetero atoms selected from the group consisting of oxygen, sulfur and nitrogen; $R_{11}$ and $R_{12}$ together can form a heterocyclic ring optionally interrupted by hetero atoms selected from the group consisting of oxygen, sulfur and nitrogen.

Illustrative but not limitative of the non-phenolic ether residues represented by R are the residues of methyl ether, ethyl ether, propyl ether, butyl ether, propyl butyl ether, ethyl butyl ether, diethyl ether, polyethylene oxide
and other such symmetrical and other unsymmetrical ethers. These non-phenolic ether residues are further illustrated by the structures given below.

TYPICAL ETHER RESIDUES REPRESENTED BY R

—CH$_2$—O—CH$_2$—
—CH$_2$—CH$_2$—O—CH$_2$—CH$_2$—
—CH$_2$—CH$_2$—CH$_2$—O—CH$_2$—CH$_2$—CH$_2$—
—CH$_2$—CH$_2$—CH$_2$—CH$_2$—O—CH$_2$—CH$_2$—CH$_2$—CH$_2$—
—CH$_2$—CH$_2$—CH$_2$—O—CH$_2$—CH$_2$—CH$_2$—CH$_2$—

—CH₂—CH₂—O—CH₂—CH₂—CH₂—CH₂—
—CH₂—CH₂—O—CH₂—CH₂—O—CH₂—CH₂—

Preferred are the ethers containing from 2 to 14 carbons, and even more preferred are the ethers containing from 2 to 6 carbon atoms.

Illustrative but not limitative of the non-phenolic thioether residues represented by R are those thioethers which result when sulfur is substituted for oxygen in the illustrated ether groups above. Preferred are the thioethers containing from 2 to 14 carbons, and even more preferred are those containing from 2 to 6 carbons.

Illustrative but not limitative of the linear and branched alkyl groups represented by R are ethyl, propyl, butyl, pentyl, hexyl, heptyl, octyl, nonyl, decyl, undecyl, dodecyl, tridecyl, pentadecyl, hexadecyl, including branched and straight chain species. Preferred are those groups having from 2 to 10 carbons; even more preferred are those containing from 2 to 8 L carbons, while most preferred are those containing 2 to 6 carbons.

Illustrative but not limitative of the cyclic alkyl groups represented by R are cyclopentane and cyclohexane, although cyclohexane is preferred.

Illustrative but not limitative of the substituted cyclic alkyl groups represented by R are dimethyl cyclohexane, 1-cyclohexylpropane, 1,4-dimethyl cyclohexane and hydrogenated bis phenol A; although hydrogenated bis phenol A and 1,4-dimethyl cyclohexane are preferred.

Illustrative but not limitative of the non-phenolic alkylaryl groups represented by R is styryl.

Illustrative but not limitative of the linear and branched alkyl groups represented individually by $R_1$, $R_2$, $R_3$, $R_4$, $R_5$, $R_6$, $R_7$, $R_8$, $R_9$, $R_{10}$, $R_{11}$ and $R_{12}$ are methyl, ethyl, propyl, butyl, pentyl, hexyl, heptyl, octyl, nonyl, decyl, undecyl and dodecyl including straight and branched chain species of the butyl, pentyl, hexyl, heptyl, octyl, nonyl, decyl, undecyl and dodecyl groups. Preferred groups are these containing from 1 to 10 carbons and most preferred are the methyl, butyl and 2-ethylhexyl groups.

Illustrative but not limitative of the cyclic alkyl groups represented individually by $R_1$, $R_2$, $R_3$, $R_4$, $R_5$, $R_6$, $R_7$, $R_8$, $R_9$, $R_{10}$, $R_{11}$ and $R_{12}$ are cyclopentyl and cyclohexyl, although cyclohexyl is preferred.

Illustrative but not limitative of the alkylaryl groups represented individually by $R_1$, $R_2$, $R_3$, $R_4$, $R_5$, $R_6$, $R_7$, $R_8$, $R_9$, $R_{10}$, $R_{11}$, and $R_{12}$ are benzyl and β-phenylethyl.

The amines useful in preparing the compounds of this invention are well known and available compounds. These include but are not limited to dimethyl amine, diethyl amine, dipropyl amine, butylamine, methyl butyl amine, methyl octyl amine, ethyl propyl amine, an amine represented by the structure

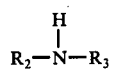

wherein $R_2$ and $R_3$ have their aforedescribed significance, and the like. It is preferred however, to use the lower molecular weight amines such as dimethylamine or diethylamine.

PREFERRED EMBODIMENTS

In a preferred embodiment of the improved method of this invention, the hydraulic fluid comprises 94.5 percent by weight of diethylene glycol bis dibutyl phosphate, 2.5 percent by weight polyalkylmethacrylate, 2.0 percent by weight epoxidized soybean oil, 0.5 percent by weight 1,2-bis(phenylmercapto) ethane and 0.5 percent by weight water.

In another preferred embodiment of the improved method of this invention, the hydraulic fluid comprises 97.5 percent by weight 1,4-hydroxymethylcyclohexyl bis-di-n-butyl phosphate and 2.5 percent by weight 3,4-epoxycyclohexylmethyl-3,4-epoxycyclohexane carboxylate.

In still another preferred embodiment of the improved method of this invention, the hydraulic fluid comprises 93.0 percent by weight diethylene glycol bis-di-2-ethylhexyl phosphate, 6.0 percent by weight polyalkylene oxide (molecular weight of 2700), 2.5 percent by weight 2-ethylhexyl-3,4-epoxycyclohexane carboxylate and 0.5 percent by weight 1,2-bis(phenylmercapto) ethane.

In the preparation of a preferred compound of this invention, diethylene glycol is added to a stoichiometric amount of phosphorus oxychloride over a period of about one hour at 500 to 200 mm, and preferably 300 mm Hg. absolute pressure, at 20°-25° C. The reaction mass is then stirred at 20°-25° C. for 2 hours at 200 to 50 mm. Hg. absolute pressure.

The entire chloridate batch is then transferred and added to the indicated amounts of butyl alcohol over a period of about 1 hour at 20°-25° C. and then stirred for about 2 hours at this temperature range.

Excess butyl alcohol and HCl are then separated from the crude ester by distillation, at 25 to 30 mm. Hg. absolute. The crude ester is then neutralized at 10° to 15° C. by ammonia addition. The neutralized ester slurry is then dissolved into water and washed at 25° C. The ester layer is vacuum steamed and water washed to neutrality. After dehydration, the final product (diethylene glycol-bis-dibutyl phosphate) is filtered through a filter aid.

In conducting the preparation of these compounds, care must be exercised to use equipment which is constructed of materials which are resistant to the corrosive alcoholic-HCl environment. Preferred materials of construction are stainless steel; however, various materials and protective coatings will be apparent to those skilled in the art, such as glass-lined reactors, ceramic reactors, etc.

In the preparation of another preferred compound of this invention, hydrogenated bis phenol A is reacted with phosphorous oxychloride to form the phosphorochlorodate, which is then reacted with 2-ethyl hexanol to form hydrogenated bis phenol A bis 2-ethylhexyl phosphate. The reaction procedure being essentially the same as in the above-described preparation.

In the preparation of another preferred compound of this invention, 1,4-dihydroxymethyl cyclohexane is reacted with phosphorous oxychloride to form the phosphorochlorodate, which is then reacted with an equal molar mixture of methyl amine and ethyl amine to form the amidate.

In the preparation of another preferred compound of this invention, diethylene glycol is reacted with phosphorous oxychloride to form the phosphorochlorodate, which is then reacted with an equal molar mixture of butyl alcohol and 2-ethylhexyl alcohol.

This invention is further illustrated by, but not limited to, the following examples.

EXAMPLES

Preparation of:

1. Diethylene glycol bis phosphorodichlorodate

To a suitable reactor was charged 307 grams of phosphorous oxychloride. The reactor was equipped with an agitator, dropping funnel, thermometer and an ice water condenser. The temperature of the phosphorous oxychloride was reduced to 20° C. and the pressure was reduced to 500 mm. Hg. 106 grams of diethylene glycol was added over 4 hours, keeping the temperature 20° C. and over the course of the addition reducing the pressure to 80 mm. Hg. The product was 333.5 grams of diethylene glycol bis phosphorodichlorodate. This is used as a reactant in Example 2 which follows.

2. Diethylene glycol bis dibutyl phosphate

To a suitable reactor was charged 741.2 grams of n-butanol and the temperature was reduced to 20° C. With stirring and maintaining a temperature 20° C., 333.5 grams of diethylene glycol bis phosphorodichlorodate was added over 1–2 hours. After the addition the reaction mixture was allowed to stir an additional 16 hours. To the crude reaction mass was charged 350 grams of 50% sodium hydroxide and 300 milliliters of water, keeping the temperature less than 30° C. The organic layer was separated and its pH was adjusted to 8.5–9.5. The excess butanol was steam distilled off. The remaining crude product was washed until neutral with water and dehydrated under vacuum to a maximum temperature of 110° C. The product was 355 grams of diethylene glycol bis dibutyl phosphate.

| | |
|---|---|
| Specific gravity, 25° C. | 1.0751 |
| Refractive Index | 1.4400 |
| Acidity (TAN) | 0.02 NN |
| Viscosity at 38° C. | 14.5 centistoke |
| at 99° C. | 4.5 centistoke |

3. Diethylene glycol bis tetramethyl phosphorodiamidate

To a suitable reactor equipped with a stirrer, condenser, dropping funnel and a thermometer was charged 721 grams of a 25% aqueous solution of dimethylamine. With temperature being maintained at 35–40° C., simultaneously was added 333 grams of diethylene glycol bis phosphorodichlorodate and 320 grams of 50% sodium hydroxide over 3–4 hours. After the addition was complete the aqueous layer was removed. The organic layer was washed until neutral with water, dehydrated under vacuum to 110° C. and filtered. The product was 175 grams of diethylene glycol bis tetramethyl phosphorodiamidate.

| | |
|---|---|
| Specific gravity, 25° C. | 1.1486 |
| Refractive Index | 1.4632 |
| Acidity (TAN) | 0.06 NN |
| Viscosity at 38° C. | 18.8 centistoke |
| at 99°C. | 4.3 centistoke |

4. Diethylene glycol bis di-2-ethylhexyl phosphate

Same procedure as (2) except substitute 2-ethylhexanol for butanol. The product was 488 grams of diethylene glycol bis di-2-ethylhexyl phosphate.

| | |
|---|---|
| Specific gravity, 25° C. | 0.9944 |
| Refractive Index, 25° C. | 1.4495 |
| Acidity (TAN) | 0.03 |
| Viscosity at 38° C. | 36.0 centistoke |
| at 99° C. | 6.25 centistoke |

5. Bis(1,4-cyclohexanedimethyl)phosphorodichlorodate

To a suitable reactor which was equipped with an agitator, dropping funnel, thermometer and an ice water cooled condenser, was charged 920 grams of phosphorous oxychloride. The stirred reaction mass was cooled to 20° C. and the pressure was reduced to 500 mm Hg. Then 432 grams of 1,4-cyclohexanedimethanol was added over 4 hours, keeping the temperature 20° C. and over the course of the addition reducing the pressure to 80 mm. Hg. The product was 1102 grams of bis(1,4-cyclohexanedimethyl)phosphorodichlorodate.

6. 1,4-di-hydroxymethyl cyclohexyl bis di-2-ethylhexyl phosphate

Same procedure as (2) except for raw material changes. The yield was 73% by weight based on phosphorochlorodate.

| | |
|---|---|
| Specific gravity, 25° C. | 0.9925 |
| Refractive Index, 25° C. | 1.4585 |
| Acidity (TAN) | 0.02 |
| Viscosity at 38° C. | 103. centistoke |
| at 99° C. | 11.3 centistoke |

7. 1,4-di-hydroxymethyl cyclohexyl bis di n-butyl phosphate

Same procedure as (2) except for raw material changes. The yield was 74% by weight based on phosphorochlorodate.

| | |
|---|---|
| Specific Gravity, 25° C. | 1.0061 |
| Refractive Index, 25° C. | 1.4530 |
| Acidity (TAN) | 0.01 |
| Viscosity at 38° C. | 35.8 centistoke |
| at 99° C. | 6.5 centistoke |

8. 1,4-di-hydroxymethylcyclohexyl bis di-cyclohexyl phosphate

Same procedure as (2) except for raw material changes. The yield was 12% by weight based on phosphorochlorodate.

| | |
|---|---|
| Acidity (TAN) | 0.06 |
| Viscosity at 99° C. | 59.0 centistoke |

9. 1,4-di-hydroxymethyl cyclohexyl bis tetramethyl phosphorodiamidate

Same procedure as (3) except for raw material changes. The yield was 74% by weight based on phosphorochlorodate.

| | |
|---|---|
| Specific Gravity, 25° C. | 1.0756 |
| Refractive Index, 25° C. | 1.4722 |
| Acidity (TAN) | 0.02 NN |
| Viscosity at 38° C. | 72. centistoke |
| at 99° C. | 11.4 centistoke |

10. Hydrogentated bisphenol A bis phosphorodichlorodate

Same procedure as (1) except raw material changes. The yield was 97% by weight based on phosphorochlorodate.

11. Hydrogenated bisphenol A bis tetramethyl phosphorodiamidate

Same procedure as (3) except for raw material changes. The yield was 74% by weight based on phosphorochlorodate of a yellow solid.

12. Diethylene glycol bis(N-methyl-N-n-butyl N'-methyl n'-n' butyl phosphorodiamidate Same procedure as (3) except N-methyl-N-n-butylamine is used for the 25% aqueous solution of dimethylamine.

13. 1,4-di-hydroxymethyl cyclohexyl bis (n-butyl,-2-ethyl-hexyl phosphate)

The same procedure as (2) except an equimolar mixture of n-butanol and 2-ethylhexanol is used.

14. Thiodiethanol bis phosphorodichlorodate

The same procedure as (1) except thiodiethanol is used instead of diethylene glycol.

15. Thiodiethanol bis dibutyl phosphate

The same procedure as (2) is used except thiodiethanol bis phosphorodichlorodate replaces the diethylene glycol bis phosphorodichlorodate.

16. Thiodiethanol bis (N-methyl-N-n-butyl N'-methyl-N'-n' butyl phosphorodiamidate)

The same procedure as (3) is used with the product of 14 reacting with N-methyl-N-n-butylamine.

17. Diethylene glycol bis 2-ethylhexyl-n-butyl phosphate

About 1000 grams of an equimolar mixture of n-butanol and 2-ethylhexanol are charged to a reactor. About 700 grams of diethylene glycol bis phosphorochlorodate are added over 1-2 hours with stirring and while maintaining the temperature below about 20° C. After the addition is completed, the reaction mixture is allowed to stir for an additional 16 hours. About 350 grams of 50% sodium hydroxide and 300 grams of water are then charged to the reactor with stirring continued and while maintaining the temperature of the reactor contents below about 30° C. The organic layer is allowed to separate from the aqueous layer which is discarded. The pH of the organic layer is adjusted to 8.5–9.5. The excess alcohol is distilled off, and the remaining crude product washed until neutral with water. The washed product (diethylene glycol bis 2-ethylhexyl n-butyl phosphate) is finally dehydrated under vacuum to a maximum pot temperature of 110° C.

The compounds of this invention are useful as hydraulic fluids either with or without additives. When used as hydraulic fluids, they are used in conjunction with a hydraulic system, which simply stated, is a system for transmitting force from one point to another utilizing a hydraulic fluid as the force transmitting medium. A simple hydraulic system consists of (1) a reservoir to hold the fluid, (2) a pump or other source of pressure, (3) piping to transfer the fluid from place to place, (4) valves or other means of control, (5) an element to convert pressure to motion, such as a motor or actuator, and (6) a hydraulic fluid; wherein the reservoir is connected to the pump and supplies hydraulic fluid to it, the piping is connected at one end to the pump and at the other end to the valve, with the valve connected by additional piping to the element such that pressure generated by the pump is transmitted through the hydraulic fluid, in an amount controlled by the valve, to the element.

The most desirable fluids for use a hydraulic fluids are those which are fire resistant and have adequate temperature-viscosity and lubricating properties, i.e., the fluids must not get too thin at higher temperatures nor too thick at low temperatures; and must also be able to provide minimal lubrication over the range of temperatures at which they are used. They must also be noncorrosive to the system in which they are being used. The properties of typical compounds of this invention are shown in Tables I and II. These tables show that the compounds of this invention are characterized by viscosity, flammability; density, acidity, and corrosivitiy properties which render them desirable as hydraulic fluids.

TABLE I

PHYSICAL PROPERTIES OF TYPICAL NON-PHENOLIC PHOSPHATE ESTERS AND AMIDATES

| | VISCOSITY | | Auto Ignition Temperature ° C. | Density g/cc ° C. | Acidity TAN |
|---|---|---|---|---|---|
| | 38° C. | 99° C. | | | |
| Diethyl glycol Bis dibutyl phosphate | 14.5 centistokes | 4.7 centistokes | 327 | 1.0751 | 0.02 |
| Diethyl glycol Bis dimethyl phosphoro amidate | 18.8 centistokes | 4.3 centistokes | 371 | 1.1486 | 0.06 |
| Diethyl glycol Bis 2 ethylhexyl phosphate | 36 centistokes | 6.3 centistokes | 346 | 0.9944 | 0.03 |
| 1,4 dihydroxy methyl cyclohexyl Bis dibutyl phosphate | 35.8 centistokes | 6.5 centistokes | 413 | 1.0061 | 0.01 |

TABLE II

ASTM oxidation-corrosion tests conducted at 121° C., 5 liter/hour air, 168 hours

| COMPOUND | Metal Loss or Gain (Milligram/Square Centimeter) | | | | | % change in 38° C. viscosity | Coke | Sludge |
|---|---|---|---|---|---|---|---|---|
| | mg. | Al. | Cd. | Fe. | Cu. | | | |
| Diethyl glycol Bis dimethyl phosphoroamidate | −3.09 | −0.01 | −0.17 | −0.01 | −1.87 | +76 | None | None |
| Diethyl glycol Bis dibutyl phosphate | −1.23 | +0.01 | −2.93 | −0.05 | −2.66 | +6 | None | None |
| Diethyl glycol Bis 2-ethylhexyl phosphate | −0.74 | +0.01 | −0.74 | −0.01 | −3.33 | +121 | None | None |
| 1,4 dihydroxy methyl cyclohexyl Bis-dibutyl phosphate | −0.20 | +0.02 | −0.29 | −0.05 | −12.6 | +116 | None | None |

While the properties shown in Tables I and II render these compounds useful as hydraulic fluids, since they fulfill the normal criteria for such use, further improvements of particular properties may be desired. Therefore, it is contemplated that the compounds of this invention be utilized either alone, in admixture with other hydraulic fluid compounds, or with various additives.

The number and purposes of additives which can be used with hydraulic fluids are infinite and the use of the compounds of this invention either alone or with any additive or combination of additives is contemplated as within the scope of this invention. The preferred uses of the compounds of this invention, however, are in conjunction with additives to further inhibit corrosion, improve viscosity index, to improve pour point and to improve high temperature oxidative stability. Examples of preferred embodiments are given in Table III which shows typical hydraulic fluid formulations of this invention.

TABLE III
TYPICAL HYDRAULIC FLUID FORMULATIONS

FLUID NO. 1:
| | |
|---|---|
| 94.5% by weight | diethylene glycol bis dibutyl phosphate |
| 2.5% by weight | polyalkylmethacrylate |
| 2.0% by weight | epoxidized soybean oil |
| 0.5% by weight | 1,2-bis(phenylmercapto)ethane |
| 0.5% by weight | Water |

FLUID NO. 2:
| | |
|---|---|
| 95.0% by weight | diethylene glycol bis dibutyl phosphate |
| 2.5% by weight | polyalkylmethacrylate |
| 2.0% by weight | epoxidized soybean oil |
| 0.5% by weight | 1,2-bis(phenylmercapto)ethane |

FLUID NO. 3:
| | |
|---|---|
| 93.0% by weight | diethylene glycol bis-di-2-ethylhexyl phosphate |
| 6.0% by weight | polyalkylene oxide (m.w. 2700) |
| 2.5% by weight | 2-ethylhexyl-3,4-epoxycyclohexane carboxylate |
| 0.5% by weight | 1,2-bis(phenylmercapto)ethane |

FLUID NO. 4:
| | |
|---|---|
| 97.5% by weight | diethylene glycol bis-di-2-ethylhexyl phosphate |
| 2.5% by weight | 2-ethylhexyl-3,4-epoxycyclohexane carboxylate |

FLUID NO. 5:
| | |
|---|---|
| 97.5% by weight | 1,4-hydroxymethylcyclohexyl bis-di-n-butyl phosphate |
| 2.5% by weight | 3,4-epoxycyclohexylmethyl-3,4-epoxycyclohexane carboxylate |

FLUID NO. 6:
| | |
|---|---|
| 94.0% by weight | diethylene glycol bis-tetramethyl phosphoroamidate |
| 2.5% by weight | polyalkylmethacrylate |
| 3.0% by weight | epoxidized soybean oil |
| 0.5% by weight | 1,2-bis(phenylmercapto)ethane |

FLUID NO. 7:
| | |
|---|---|
| 97.2% by weight | 1,4-hydroxymethylcyclohexyl bis tetramethyl phosphoroamidate |
| 2.8% by weight | n-butyl-3,4-epoxycyclohexane carboxylate |

Although the invention has been described in terms of specified embodiments which are set forth in considerable detail, it should be understood that this is by way of illustration only and that the invention is not necessarily limited thereto since alternative embodiment and operating techniques will become apparent to those skilled in the art in view of the disclosure. Accordingly, modifications are contemplated which can be made without departing from the scope of the described invention.

What is claimed is:

1. A method of transmitting force from one point to another utilizing a hydraulic fluid as the force transmitting medium, the improvement which comprises utilizing as said force transmitting medium at least one compound represented by the structure

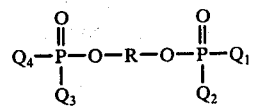

where $Q_1$ is $-O-R_1$ or

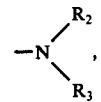

$Q_2$ is $-O-R_4$ or

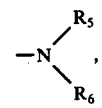

$Q_3$ is $-O-R_7$ or

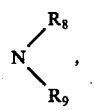

$Q_4$ is $-O-R_{10}$ or

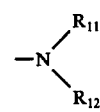

R is nonphenolic alkylaryl, R containing from 1 to 16 carbon atoms; provided that the $-O-R-O-$ portion of the structure is non-phenolic; $R_1$, $R_2$, $R_3$, $R_4$, $R_5$, $R_6$, $R_7$, $R_8$, $R_9$, $R_{10}$, $R_{11}$ and $R_{12}$ each contain from 1-12 carbons and are individually selected from the group consisting of linear alkyl, branched alkyl, cyclic alkyl, nonphenolic alkylaryl, or substituted cyclic alkyl and can be the same or different in any combination.

2. The method of claim 1 wherein $Q_1$ is

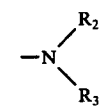

$Q_2$ is

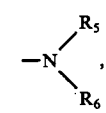

$Q_3$ is

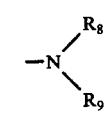

and $Q_4$ is

3. In a method of transmitting force from one point to another utilizing a hydraulic fluid as the force transmitting medium, the improvement which comprises utilizing hydrogenated bisphenol A bis tetramethyl phosphorodiamidate as said force transmitting medium.

4. In a method of transmitting force from one point to another utilizing a hydraulic fluid as the force transmitting medium, the improvement which comprises utilizing diethylene glycol bis tetramethyl phosphorodiamidate as said force transmitting medium.

* * * * *